US 9,089,422 B2

(12) United States Patent
Ryan et al.

(10) Patent No.: US 9,089,422 B2
(45) Date of Patent: Jul. 28, 2015

(54) MARKERS FOR PROSTHETIC HEART VALVES

(75) Inventors: Timothy R. Ryan, Shorewood, MN (US); Charles Tabor, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 23 days.

(21) Appl. No.: 12/358,765

(22) Filed: Jan. 23, 2009

(65) Prior Publication Data
US 2009/0192591 A1 Jul. 30, 2009

Related U.S. Application Data

(60) Provisional application No. 60/062,207, filed on Jan. 24, 2008.

(51) Int. Cl.
*A61F 2/82* (2013.01)
*A61F 2/24* (2006.01)
*A61F 2/95* (2013.01)

(52) U.S. Cl.
CPC ............. *A61F 2/2412* (2013.01); *A61F 2/2436* (2013.01); *A61F 2/2418* (2013.01); *A61F 2002/9505* (2013.01); *A61F 2002/9511* (2013.01); *A61F 2250/0098* (2013.01)

(58) Field of Classification Search
CPC .............. A61F 2/91; A61F 2250/0097; A61F 2250/0098
USPC ............ 623/1.24, 1.26, 2.11, 2.18, 1.34, 1.43
See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |

(Continued)

FOREIGN PATENT DOCUMENTS

| CN | 2007-100074433 | 8/2007 |
| DE | 195 32 846 | 3/1997 |

(Continued)

OTHER PUBLICATIONS

U.S. Appl. No. 12/476,702, filed Jun. 2, 2009.

(Continued)

*Primary Examiner* — Thomas J Sweet
*Assistant Examiner* — Seema Mathew

(57) ABSTRACT

A replacement prosthetic heart valve for engagement with a structure of an original prosthetic heart valve that includes at least one visually detectable marker. The replacement heart valve includes a stent structure having a generally tubular body portion and at least one visually detectable marker on a portion of the stent structure, and at least two leaflets attached within the interior area of the tubular body portion of the stent structure. At least one visually detectable marker of the stent structure is alignable with at least one visually detectable marker of the original prosthetic heart valve.

17 Claims, 3 Drawing Sheets

(56) References Cited

U.S. PATENT DOCUMENTS

| | | |
|---|---|---|
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,232,445 A | 8/1993 | Bonzel |
| 5,272,909 A | 12/1993 | Nguyen et al. |
| 5,295,958 A | 3/1994 | Shturman |
| 5,320,100 A * | 6/1994 | Herweck et al. ............. 600/431 |
| 5,327,774 A | 7/1994 | Nguyen et al. |
| 5,332,402 A | 7/1994 | Teitelbaum |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,702,368 A | 12/1997 | Stevens et al. |
| 5,713,953 A | 2/1998 | Vallana et al. |
| 5,716,417 A | 2/1998 | Girard et al. |
| 5,741,327 A * | 4/1998 | Frantzen ..................... 623/1.34 |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A * | 9/1999 | Leonhardt et al. ............ 623/1.24 |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,334,871 B1 * | 1/2002 | Dor et al. ..................... 623/1.34 |

(56) References Cited

U.S. PATENT DOCUMENTS

| | | |
|---|---|---|
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 * | 9/2002 | Schreck .................. 623/2.18 |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,623,518 B2 * | 9/2003 | Thompson et al. .......... 623/1.11 |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,476 B2 * | 12/2005 | McGuckin, Jr. et al. .... 623/2.36 |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,331,991 B2 * | 2/2008 | Kheradvar et al. .......... 623/1.22 |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,510,572 B2 * | 3/2009 | Gabbay .................. 623/2.11 |
| 7,544,206 B2 | 6/2009 | Cohn et al. |
| 7,556,646 B2 | 7/2009 | Yang et al. |
| 7,771,467 B2 * | 8/2010 | Svensson .................. 623/1.26 |
| 7,913,371 B2 * | 3/2011 | Klocke et al. .................. 29/453 |
| 8,002,818 B2 * | 8/2011 | Bregulla .................. 623/1.16 |
| 8,025,694 B2 * | 9/2011 | Strauss et al. .................. 623/1.16 |
| 8,303,653 B2 * | 11/2012 | Bonhoeffer et al. .......... 623/1.26 |
| 8,308,798 B2 * | 11/2012 | Pintor et al. .................. 623/2.18 |
| 8,317,858 B2 * | 11/2012 | Straubinger et al. .......... 623/2.12 |
| 8,322,593 B2 * | 12/2012 | Wack ............................ 228/170 |
| 8,348,995 B2 * | 1/2013 | Tuval et al. .................... 623/2.1 |
| 8,366,768 B2 * | 2/2013 | Zhang .......................... 623/2.11 |
| 8,414,643 B2 * | 4/2013 | Tuval et al. ..................... 623/2.1 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |

(56) References Cited

U.S. PATENT DOCUMENTS

| | | |
|---|---|---|
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0105511 A1* | 6/2003 | Welsh et al. ............ 623/1.15 |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2004/0034411 A1 | 2/2004 | Quijano et al. |
| 2004/0039436 A1* | 2/2004 | Spenser et al. ............ 623/1.13 |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty et al. |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz et al. |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060025 A1* | 3/2005 | Mackiewicz et al. ........ 623/1.34 |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137689 A1* | 6/2005 | Salahieh et al. ............ 623/2.11 |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1* | 3/2006 | Revuelta et al. ............ 623/2.18 |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0195184 A1* | 8/2006 | Lane et al. ............ 623/2.38 |
| 2006/0206192 A1 | 9/2006 | Tower et al. |
| 2006/0206202 A1 | 9/2006 | Bonhoeffer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |

(56) References Cited

U.S. PATENT DOCUMENTS

| | | |
|---|---|---|
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2006/0287717 A1* | 12/2006 | Rowe et al. .................. 623/2.11 |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0156230 A1* | 7/2007 | Dugan et al. .................. 623/1.16 |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1* | 10/2007 | Birdsall ........................ 623/1.26 |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0266542 A1* | 11/2007 | Melsheimer ................ 29/522.1 |
| 2007/0288000 A1 | 12/2007 | Bonan |
| 2007/0293942 A1* | 12/2007 | Mirzaee ........................ 623/2.11 |
| 2007/0299514 A1 | 12/2007 | Colvin et al. |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | DiNucci et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1* | 4/2008 | Styrc et al. .................... 623/2.18 |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154356 A1 | 6/2008 | Obermiller et al. |
| 2008/0161910 A1 | 7/2008 | Revuelta et al. |
| 2008/0161911 A1* | 7/2008 | Revuelta et al. ............. 623/2.17 |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0275540 A1* | 11/2008 | Wen ............................. 623/1.26 |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0240264 A1 | 9/2009 | Tuval et al. |
| 2009/0240320 A1 | 9/2009 | Tuval |
| 2009/0287299 A1 | 11/2009 | Tabor et al. |
| 2010/0011564 A1 | 1/2010 | Millwee et al. |
| 2010/0018447 A1 | 1/2010 | Holecek et al. |
| 2010/0023120 A1 | 1/2010 | Holecek et al. |
| 2010/0036484 A1 | 2/2010 | Hariton et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0312333 A1* | 12/2010 | Navia et al. .................. 623/2.36 |
| 2014/0200656 A1* | 7/2014 | Thomas et al. ............... 623/1.34 |
| 2015/0018934 A1* | 1/2015 | Pacetti ......................... 623/1.16 |
| 2015/0045875 A1* | 2/2015 | Hingston et al. ............. 623/1.34 |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1239795 | 9/2002 |
| EP | 1255510 | 11/2002 |
| EP | 0937439 B1 | 9/2003 |
| EP | 1340473 | 9/2003 |
| EP | 0819013 | 6/2004 |
| FR | 2788217 | 12/1999 |
| GB | 2056023 | 3/1981 |
| GB | 2398245 | 8/2004 |
| GB | 2433700 | 12/2007 |
| WF | 02/41789 | 5/2002 |
| WF | 02/47575 | 6/2002 |
| WO | 91/17720 | 11/1991 |
| WO | 93/01768 | 2/1993 |
| WO | 95/29640 | 11/1995 |
| WO | 98/14137 | 4/1998 |
| WO | 98/29057 | 7/1998 |

(56) References Cited

FOREIGN PATENT DOCUMENTS

| | | | |
|---|---|---|---|
| WO | 99/33414 | 7/1999 | |
| WO | 00/41652 | 7/2000 | |
| WO | 00/44313 | 8/2000 | |
| WO | 00/47136 | 8/2000 | |
| WO | 00/47139 | 8/2000 | |
| WO | 01/35870 | 5/2001 | |
| WO | 01/49213 | 7/2001 | |
| WO | WO 0147438 A1 * | 7/2001 | |
| WO | 01/54625 | 8/2001 | |
| WO | 01/62189 | 8/2001 | |
| WO | 01/64137 | 9/2001 | |
| WO | 01/76510 | 10/2001 | |
| WO | 02/22054 | 3/2002 | |
| WO | 02/36048 | 5/2002 | |
| WO | 02/43620 | 6/2002 | |
| WO | 02/49540 | 6/2002 | |
| WO | 03/003943 | 1/2003 | |
| WO | 03/003949 | 1/2003 | |
| WO | 03/011195 | 2/2003 | |
| WO | 03/030776 | 4/2003 | |
| WO | 2004/019811 | 3/2004 | |
| WO | 2004/019825 | 3/2004 | |
| WO | 2004/023980 | 3/2004 | |
| WO | 2004/041126 | 5/2004 | |
| WO | 2004/058106 | 7/2004 | |
| WO | 2004/089250 | 10/2004 | |
| WO | 2005/004753 | 1/2005 | |
| WO | 2005/027790 | 3/2005 | |
| WO | 2005/046528 | 5/2005 | |
| WO | 2007/054015 | 5/2007 | |
| WO | 2007/130537 | 11/2007 | |
| WO | 2007130537 | * 11/2007 | A61F 2/24 |
| WO | 2008/047354 | 4/2008 | |
| WO | 2008/100599 | 8/2008 | |
| WO | 2008/150529 | 12/2008 | |
| WO | 2009/002548 | 12/2008 | |
| WO | 2009/029199 | 3/2009 | |
| WO | 2009/042196 | 4/2009 | |
| WO | 2009/045338 | 4/2009 | |
| WO | WO 2009/042196 A2 | 4/2009 | |
| WO | 2009/061389 | 5/2009 | |
| WO | 2009/091509 | 7/2009 | |

OTHER PUBLICATIONS

U.S. Appl. No. 12/711,289, filed Feb. 24, 2010.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. Volume II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.

(56) References Cited

OTHER PUBLICATIONS

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Walther, et al., "Valve-in-a-Valve Concept for Transcatheter Minimally Invasive Repeat Xeongraft Implantation," JACC, vol. 50, No. 1, 2007, pp. 56-60.

Webb, et al., "Percutaneous Aortic Valve Implantation Retrograde from the Femoral Artery," Circulation (2006), 113;842-850.

Moss, et al., "Role of Echocardiography in Percutaneous Aortic Valve Implantation," JACC, vol. 1, No. 1, 2008, p. 15-24.

Pasupati, et al., "Transcatheter Aortic Valve Implantation Complicated by Acute Structural Valve Failure Requiring Immediate Valve Implantation,"Heart, Lung and Circulation, 2010, doi;10.1016/j.hlc.2010.5.006.

European Patent Office Communication in Application No. 09 704 087.7-2320, Dated Nov. 30, 2012, 5 pages.

\* cited by examiner

MARKERS FOR PROSTHETIC HEART VALVES

CROSS-REFERENCE TO RELATED APPLICATION

The present application claims priority to U.S. Provisional Application No. 61/062,207, filed Jan. 24, 2008, and titled "Delivery Systems and Methods of Implantation for Prosthetic Heart Valves", the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a desire to be able to easily and accurately position percutaneously delivered replacement valves within a previously implanted valve. In particular, it would be advantageous to provide a replacement valve and corresponding delivery system that facilitates proper positioning of the replacement valve with respect to certain features of a heart valve that was previously implanted, while viewing the valve from outside the patient's body.

SUMMARY

The prosthetic valves of the invention are configured to provide complimentary features that promote optimal placement of a replacement heart valve within their interior areas. Such a placement of a replacement heart valve can be performed percutaneously or minimally invasively. The features of the invention can be used for aortic valve, mitral valve, pulmonic valve, venous, and/or tricuspid valve replacement. In some embodiments, the replacement heart valves of the invention are highly amenable to transvascular delivery using a transapical approach (either with or without cardiopulmonary bypass and either with or without rapid pacing). The methodology associated with the present invention can be repeated multiple times, such that several prosthetic heart valves of the present invention can be mounted on top of or within one another, if necessary or desired.

The replacement heart valves of the invention each include a compressible stent or frame to which a valve structure is attached. The stents of the invention include a wide variety of structures and features that can be used alone or in combination with features of other stents of the invention. In particular, these stents can be provided with a number of different docking and/or anchoring structures that are conducive to percutaneous delivery thereof. Many of the structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach.

When delivering a replacement valve in accordance with the invention, it is rotatable in vivo to allow the valve to be positioned in a desired orientation. In one embodiment of the invention, a surgically implanted valve is provided with at least one marking or some type of indicia that is radiopaque, echogenic, and/or has some other characteristic that allows it to be viewed from outside the patient's body. The marking or indicia can be provided so that it provides a positive indication of the position and orientation of the stent frame. The replacement stented valve can be provided with markings that correspond to the markings on the surgically implanted valve. The replacement valve can further include a compliant skirt that is designed to function both as a sealing ring and as a visual indicator of the positioning and seating of the valve during and after implantation.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
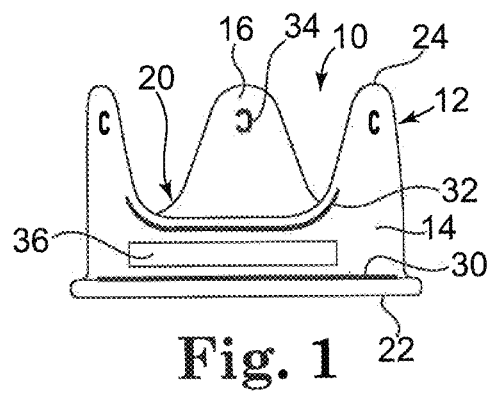
FIG. 1 is a front view of a prosthetic heart valve frame.

Referring now to the Figures, wherein the components are labeled with like numerals throughout the several Figures, and initially to FIG. 1, one embodiment of an exemplary prosthetic heart valve 10 is illustrated. This valve 10 is a typical configuration of a valve that can be implanted within the heart of a patient, such as by suturing or otherwise securing the valve 10 into the area of a native heart valve of a patient. The native heart valves referred to herein can be any of the human heart valves (i.e., mitral valve, tricuspid valve, aortic valve, or pulmonary valve), wherein the type and orientation of an implanted (e.g., surgically implanted) prosthetic heart valve 10 will correspond with the particular form, shape, and function of the native heart valve in which it is implanted. Although valve 10 would typically include multiple leaflets attached within its interior area, such leaflets are not shown in this figure for illustration clarity purposes.

Valve 10 generally includes a valve structure 12 including a stent structure 14 from which multiple stent posts or commissure posts 16 extend. All or a portion of the valve structure 12, including the stent structure 14 and stent posts 16, can be covered by a flexible covering, which may be a tissue, polymer, fabric, cloth material, or the like to which leaflets (not shown) of the heart valve 10 are attached, such as by sewing. The stent structure 14 may alternatively be a wire form. Further, as is known in the art, the internal structure of each of the stent posts 16 can be formed of a stiff but somewhat resiliently bendable material. This construction allows the stent posts 16 to be moved from the orientation shown in FIG. 1 to a deflected orientation by the application of an external force. Once this external force is removed or reduced, the stent posts 16 can then move back toward the orientation shown in FIG. 1. Alternatively, the stent posts can be angled at least slightly toward or away from a central axis of the valve 10.

The valve structure 12 is generally tubular in shape, defining an internal area 20 (referenced generally) that extends from an inflow end 22 to an outflow end 24. The internal area 20 is essentially surrounded by the valve structure 12, and the leaflets attached within the valve structure 12 selectively allow for fluid flow into and out of the lumen of the natural heart valve in which it is implanted. That is, the internal area 20 is alternatively open and closed to the lumen of the natural heart valve in which it is inserted via movement of leaflets. In some patients, the prosthetic heart valve 10 will be implanted using typical surgical techniques, whereby the stent ring 14 is sewn or attached to the annulus or valvular rim of the native heart valve. Alternatively, the prosthetic valve can be placed in the patient using minimally invasive techniques for holding the valve in place, such as U-clips, for example, or a wide variety of other techniques and features used for minimally invasive and/or percutaneous implantation of the initial prosthetic heart valve.

The prosthetic heart valves (e.g., heart valve 10 and replacement valve 50 that will be discussed below) used in accordance with the devices and methods of the invention may include a wide variety of different configurations, such as a prosthetic heart valve that has tissue leaflets, or a synthetic heart valve that has polymeric leaflets. In this way, the heart valves can be specifically configured for replacing any heart valve. That is, while much of the description herein refers to replacement of aortic valves, the stents (and their associated leaflets) of the invention can also generally be used for replacement of tricuspid valves, for use as a venous valve, or to replace a failed bioprosthesis, such as in the area of an aortic valve or mitral valve, for example. The replacement prosthetic heart valves of the present invention can be employed to functionally replace stentless prosthetic heart valves as well.

Referring again to FIG. 1, heart valve 10 further includes a number of markers that can help to facilitate accurate placement of a replacement heart valve within the valve structure 12, such as when the originally implanted heart valve 10 becomes deficient and needs to be replaced. In particular, heart valve 10 is provided with at least one annular marker 30 that can extend along one or more portions or the entire annular portion of a valve, at least one sinus marker 32 for placement at the sinus opening, and at least one commissure marker 34 that can be used for locating of one or more commissure posts.

In this exemplary embodiment, commissure marker 34 has a curved "c" shape, which is a directional marker that can help the clinician in determining the location of the post and also in determining whether the stent post is facing toward or away from the viewing direction. In other words, each marker 34 can advantageously be configured to be distinctly different or opposite when viewed from the front and back, due to its shape or configuration. In addition, the markers 34 are preferably made of a material that allows them to be viewed from the opposite surface of the stent post from the surface on which the marker 34 is placed (i.e., "through" the stent post) when using certain imaging techniques. Due to the directional nature of the markers, these indicia would therefore be displayed backwards or as a mirror image of the original marker when viewed from the opposite side of the commissure post. However, it is contemplated that the marker 34 will not be visible to the unassisted eye in this "backward" orientation, but that it will only be visible in this orientation when using specific visualization equipment. It is further contemplated that the marker(s) can extend through the entire thickness of the stent or that the marker(s) are provided in some other way so that they are visible from both sides, even without visualization equipment.

FIG. 1 shows an arrangement where two of the "c" shaped markers 34 are facing forward and one of the "c" shaped markers 34 is shown as being backward because it is actually being viewed through the commissure post 16. The marker 34 can instead be a different letter of the alphabet, a number, a symbol, a shape, or some other indicia or combination of different indicia. It is preferred, however, that the indicia is easily distinguishable as having a front view or position and a reverse view or position. It is further contemplated that different commissure posts 16 have a different marker or indicia so that each of the commissure posts 16 are also visually distinguishable from each other. Another marker 36 can also be provided to indicate the location in which the replacement valve 10 can "seal" into the original valve. Marker 36 can be a strip or area that is positioned generally adjacent to the member 32, as shown, and the valve 10 may include a marker 36 adjacent to each of the markers 32. That is, marker 36 may comprise multiple marker strips spaced from each other around the circumference of the valve 10, or may comprise a single continuous strip that extends all or most of the entire circumference of the valve 10. A single valve may include some or all of these different types and positions of markers.

The marker or markers provided on the heart valve can be made of a radiopaque material and/or have echogenic or other properties so that they are visible from outside the patient's body when using an appropriate imaging technique. The markers may be made of platinum iridium, tungsten, barium sulfate, other radiopaque materials, and the like. In this way, the markers can be used to view the movement of the valve while it is being implanted in the patient and can also be used to verify correct positioning of the valve.

After some period of time, it may become desirable to place or implant a replacement prosthetic heart valve relative to a previously implanted prosthetic heart valve to functionally replace the older heart valve. This may occur in cases where it is determined that a previously implanted prosthetic heart valve is functionally deficient due to one or more of a variety of factors, such as stenosis, valve failure, structural thrombosis, inflammation, valve insufficiency, and/or other medical conditions. Regardless of the cause of the deficiency, rather than removing the previously implanted prosthetic heart valve and implanting a second, similarly configured prosthetic heart valve via relatively complicated and invasive open heart surgical techniques, the methods and devices of the present invention leave the deficient previously implanted prosthetic heart valve in place (e.g., heart valve 10), and deploy a replacement heart valve so that it functionally replaces the previously implanted prosthetic heart valve. Prior to implanting the replacement valve, the leaflets of the previously implanted and deficient prosthetic heart valve can either be removed using a variety of techniques such as cutters, lasers, and the like, or the leaflets may instead be left in place within the deficient valve, where they will likely be pushed toward the walls of the vessel upon implantation of the replacement valve.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of the sinus region of the replacement valve does not interfere with native coronary flow; (6) verification that the sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

Figure 2:
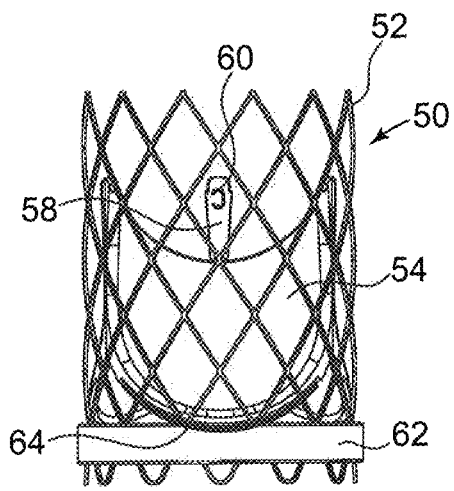
FIG. 2 is a front view of a replacement stented heart valve.
Figure 3:
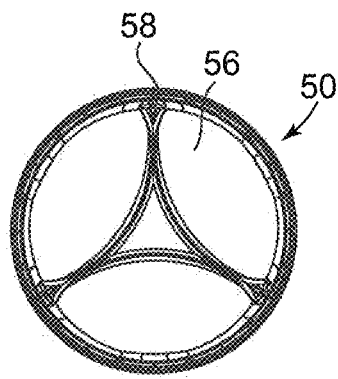
FIG. 3 is a top view of the replacement stented heart valve of FIG. 2.

FIGS. 2 and 3 illustrate one exemplary embodiment of a replacement valve 50, which generally includes a stent 52 and a valve structure 54 positioned within and attached to the stent 52. The valve 50 further includes a sealing skirt 62 adjacent to one end that extends generally around the outer periphery of the stent 52. In general, the stents described herein include a support structure comprising a number of strut or wire portions arranged relative to each other to provide a desired compressibility and strength to the heart valve. Other details of various configurations of the stents of the invention are also described below; however, in general terms, stents of the invention are generally tubular support structures, and a valve structure will be secured with this support structure to make a stented valve.

Some embodiments of the support structures of the stents described herein can be a series of wires or wire segments arranged so that they are capable of transitioning from a collapsed state to an expanded state. The stents may further include a number of individual wires formed of a metal or other material that comprise the support structure. These wires are arranged in such a way that allows for folding or compressing to a contracted state in which the internal stent diameter is greatly reduced from when it is in an expanded state. In its collapsed state, such a support structure with attached valves can be mounted over a delivery device, such as a balloon catheter, for example. The support structure is configured so that it can expand when desired, such as by the expansion of the balloon catheter. The delivery systems used for such a stent should be provided with degrees of rotational and axial orientation capabilities in order to properly position the new stent at its desired location.

The wires of the support structure of the stents in other embodiments can alternatively be formed from a shape memory material such as a nickel titanium alloy (e.g., Nitinol). With this material, the support structure is self-expandable from a contracted state to an expanded state, such as by the application of heat, energy, or the like, or by the removal of external forces (e.g., compressive forces provided by a sheath). This support structure can typically be repeatedly compressed and re-expanded without damaging the structure of the stent. In one embodiment of the invention, the stent 52 is made of a series of wires that are compressible and expandable through the application and removal of external forces, and may include a series of Nitinol wires that are approximately 0.011-0.015 inches in diameter, for example. The support structure of the stents may be laser cut from a single piece of material or may be assembled from a number of different components. For these types of stent structures, one example of a system that can be used for delivery thereof includes a catheter with a retractable sheath that covers the stent until it is to be deployed, at which point the sheath can be retracted to allow the stent to expand.

Valve structure 54 includes multiple leaflets 56 that are attached to stent features 58. Some or all of stent features 58 further include a stent marking or indicia 60, which will be discussed in further detail below. The stent features 58 may be a separate component that is secured within the stent, or the stent features 58 may actually be the general area where two leaflet pieces that are sewn to the stent form a "peak" or commissure area. The valve structures shown and described relative to the Figures are generally configured to accommodate multiple leaflets and replace a heart valve (e.g., heart valve 10) that has a corresponding number of commissure posts for a multiple-leaflet structure. The replacement prosthetic heart valves of the invention will generally include three leaflets, but can incorporate more or less than three leaflets. As referred to herein, the replacement heart valves may include a wide variety of different configurations, such as a replacement heart valve having tissue leaflets or a synthetic heart valve having polymeric, metallic, or tissue-engineered leaflets, and can be specifically configured for replacing any heart valve.

The leaflets of the valves can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films produced at Advanced Bio Prosthetic Surfaces (ABPS) of San Antonio, Tex., for example.

In more general terms, the combination of a support structure with one or more leaflets for a replacement heart valve can assume a variety of other configurations that differ from those shown and described, including any known prosthetic heart valve design. In certain embodiments of the invention, the support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacefilent", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

FIGS. 4-7 illustrate the positioning of a replacement valve 50 within the internal area 20 of heart valve 10. For illustration purposes, a portion of the stent structure 14 is removed so that that the internal area of the heart valve 10 can be viewed more clearly; however, the stent structure 14 will typically be a continuous ring structure that has previously been implanted in a patient. In one embodiment of the invention, the replacement valve 50 is delivered percutaneously to the area of the heart valve 10. If the valve 50 includes a balloon-expandable stent, this can include providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is connected to an inflation source. It is noted that if the stent being implanted is a self-expanding type of stent, the balloon would not be needed and a sheath or other restraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the replacement stent is mounted over the balloon in a contracted state to be as small as possible without causing permanent deformation of the stent structure. As compared to the expanded state, the support structure is compressed onto itself and the balloon, thus defining a decreased inner diameter as compared to its inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery.

Figure 4:
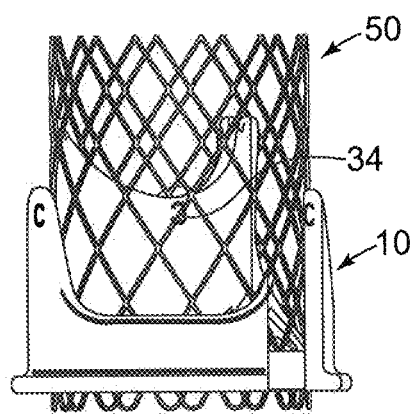
FIG. 4 is a front view of the stented valve of FIG. 2 positioned relative to the prosthetic valve frame of FIG. 1.

As described above, the heart valve 10 includes one or more markers 30, 32, 34, and/or 36, and the replacement valve 50 includes one or more radiopaque, echogenic, or MRI visible markers 60 to facilitate visual confirmation of proper placement of the replacement valve 50. The valve 50 may further include one or more markers 64, each of which extends generally along a portion of the belly of a leaflet, such as leaflet 56. In addition, the sealing skirt 62 can itself have echogenic or detectable properties for alignment with features of a heart valve 10. Further, although one of the markers 34 is shown in FIGS. 4 and 6 as an inverted "C" shape, this marker would only be visible in this configuration when using visualization techniques for detecting this marker (e.g., fluoroscopic visualization techniques and equipment), since it would not otherwise be visible to the eye through the tissue of the valve 50. Thus, in order to implant a replacement valve 50, it can be advanced using a delivery system or other surgical device and methods to the internal area 20 of the heart valve 10, One or more of the imaging techniques discussed above can then be used to orient and accurately position the replacement valve 50, where one such technique is illustrated with continued reference to FIGS. 4-7.

Figure 5:
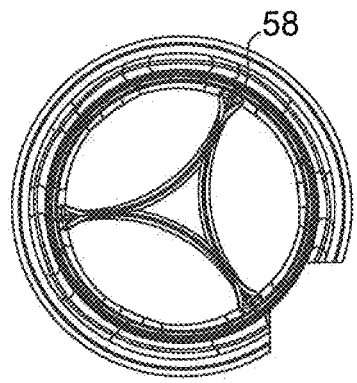
FIG. 5 is a top view of the valve and valve frame of FIG. 4.
Figure 6:
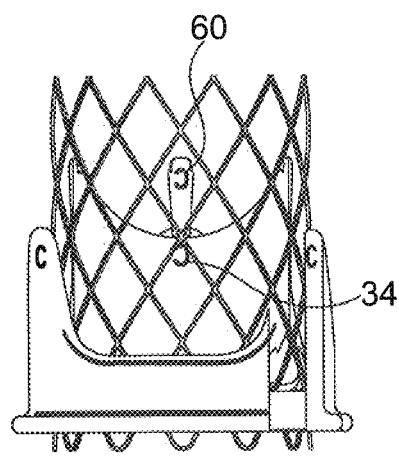
FIG. 6 is another front view of the stented valve of FIG. 2 positioned relative to the prosthetic valve frame of FIG. 1.
Figure 7:
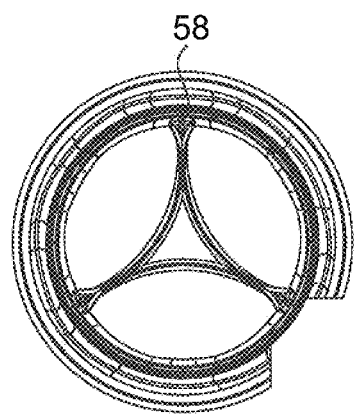
FIG. 7 is a top view of the valve and valve frame of FIG. 6.

As shown in FIGS. 4 and 5, none of the stent post markers 60 are aligned with the commissure markers 34 on the heart valve 10. Thus, the replacement valve 50 is not optimally oriented and can be rotated by the delivery system, for example, until the stent post markers 60 are aligned with the commissure markers 34, as is illustrated in FIGS. 6 and 7, and as can be verified using an imaging system that makes these markers visible to the operator of the valve delivery system. The delivery system is preferably capable of orienting the replacement valve rotationally and in a longitudinal direction relative to the heart valve in which it will be positioned. The other markers provided on the heart valve 10 can also be observed relative to markers on the replacement valve 50 to verify the proper orientation of the valve 50 relative to the valve 10. In addition or alternatively, a marker 64 of the replacement valve 50 can be aligned with a sinus marker 32 of the valve 10 and/or a marker zone 62 of the replacement valve 50 can be aligned with an annular marker 30 and/or marker 36 of the heart valve 10. In one embodiment, one or more of the markers 60, 62, 64 of the replacement valve 50 can be aligned with respective markers of the heart valve 10 (e.g., markers 34, 36, 32, respectively). Alternatively, any combination of one or more markers can be used for alignment of replacement valve 50 with features of heart valve 10.

Orientation and positioning of the replacement stented valves may be accomplished either by self-orientation of the stents (such as by interference between features of the stented valve and a previously implanted stent or valve structure) or by manual orientation of the stented valve to align its features with anatomical or previous bioprosthetic features, such as can be accomplished using fluoroscopic visualization techniques, for example. For example, when aligning the stented valves of the invention relative to native anatomical structures, they should be aligned so as to not block the coronary arteries, and native mitral or tricuspid valves should be aligned relative to the anterior leaflet and/or the trigones/commissures.

While one exemplary embodiment of a replacement valve is described above, it is understood that the stent of the replacement valve can have a structure that is at least somewhat different than that illustrated in FIG. 2. That is, stent can have the same or a different number of crowns at its opposite ends, and/or the center portion can have a more or less dense concentration of wires than either of the ends. The stent may further include a central bulbous region between the first and second ends that has a larger diameter than the first and second ends of the stent. The bulbous region can be configured to generally match the contours of the anatomy where the stent will be positioned in the patient (e.g., at the aortic valve sinus region). The stent may alternatively or additionally include flared portions that extend from opposite sides of the central portion. Such a stent may be positioned within the anatomy (e.g., the aorta) of a patient so that the flares extend into the adjacent ventricle in order to help anchor the stent in place but so that they do not disrupt the native anatomical function.

It can be advantageous for the stent delivery process that the replacement valve is retractable or partially retractable back into a sheath at any point in the process until the stent is disengaged from the delivery system. This can be useful for repositioning of the stent if it is determined that the stent has been improperly positioned relative to the patient's anatomy and/or the prosthetic heart valve into which it is being delivered. In this case, the steps described above can be repeated, using the markers as desired, until the desired positioning of the replacement valve is achieved.

Figure 8:
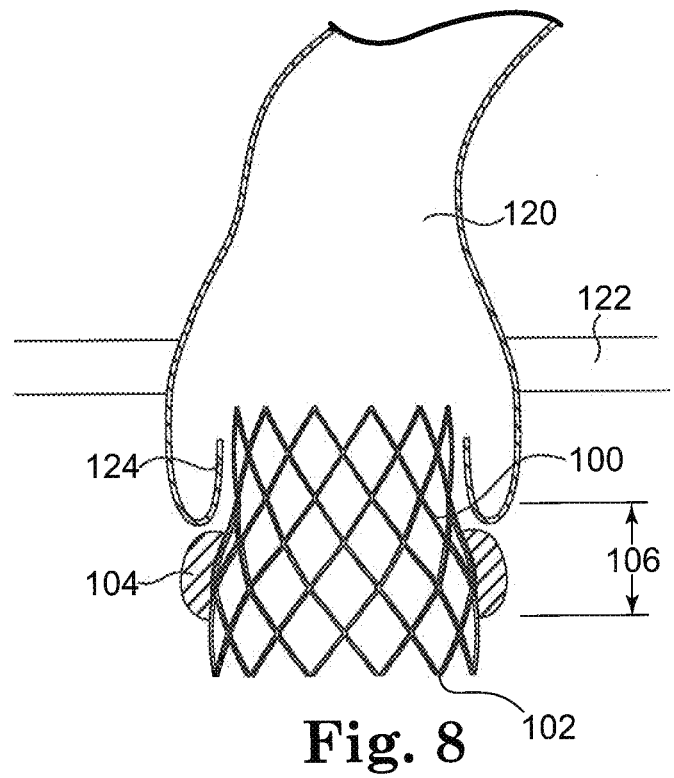
FIG. 8 is a schematic front view of a stent in a first position relative to an aortic valve.
Figure 9:
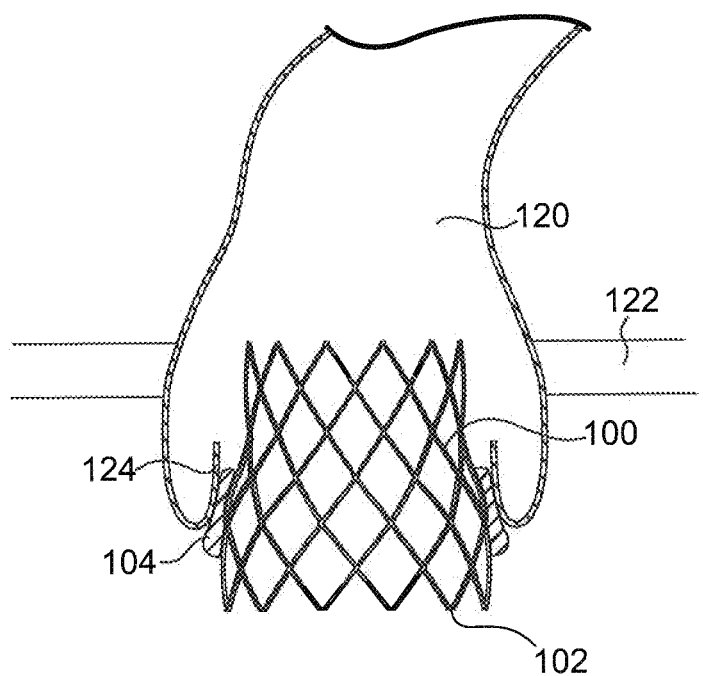
FIG. 9 is a schematic front view of the stent of FIG. 8 in a second position relative to an aortic valve.

Another embodiment of the invention is illustrated in FIGS. 8 and 9 with a stent 100 positioned relative to an aorta 120, coronary arteries 122, and native aortic valve leaflets 124. The stent 100 is generally tubular in shape and includes a series of generally flexible wires or wire segments arranged so that the stent is capable of transitioning from a collapsed state to an expanded state. The valve that would be positioned within the stent is not illustrated in these figures; however, such a valve with leaflets would be attached within the stent to provide a stented valve.

Stent 100 is illustrated as having a larger diameter at its inflow end 102 and a compliant skirt 104 positioned in the transition area between the larger and smaller diameter portions of the stent. The compliant skirt 104 preferably extends around all or most of the periphery of the stent 100 and is designed to function as either or both a sealing ring for the stent 100 and as a visual indicator of the positioning of the stent relative to the anatomy in which it is being implanted. The skirt 104 can alternatively or additionally be provided with anchoring features such as tissue ingrowth coatings or hooks that help minimize paravalvular leakage and promote anchoring of the stent 100. The skirt 104 is further provided to facilitate positioning of the implant with respect to the patient's anatomy. The skirt 104 is therefore provided with radiopaque properties, echogenic properties, and/or other visualization properties, and can be made from a fabric, polymer, wire, mesh material, gel material, or combination thereof, for example. Any of these materials can be provided with various radiopaque properties and/or additives so that the skirt 104 is viewable using chosen imaging techniques and equipment. The markers can be uniformly dispersed throughout the skirt or may alternatively or additionally be located at specific valve features such as commissures, leaflets, and the like. The skirt 104 may be made of a porous or a non-porous material. The skirt 104 is also provided with an initial shape and size that will require it to be deformed at least slightly when the stent is properly positioned relative to its target location.

As shown, the native valve leaflets 124 have been pushed toward the walls of the aorta 120 by the structure of the stent 100 as it has been positioned using some type of delivery system, such as one of the types of delivery systems discussed above. FIG. 8 illustrates an initial positioning of the stent relative to a landing zone 106. When the stent 100 is in this position, the skirt 104 is not yet in contact with the annulus of the aortic valve and the leaflets 124. The stent 100 is then moved closer to the annulus of the aorta until the skirt 104 contacts the annulus, as is shown in FIG. 9, which thereby causes the compliant skirt 104 to deform. In order to provide a uniform seal around annulus, it is preferable that all or most of the periphery of the skirt 104 deforms at least slightly when it is pressed against the annulus. The circumferential positioning of the skirt 104 also provides the clinician with the ability to identify whether or not the replacement stented valve is seated normal to the longitudinal axis of the aorta 120 to thereby minimize the chances for paravalvular leakage, heart block, and/or migration. The deformation of the compliant skirt 104 therefore preferably provides a positive visual indication of the correct placement and proper axial rotational alignment of the stent.

The skirt 104 may be provided with a specific shape and/or size that can be measured and/or quantified in its initial condition. A target amount of deformation can be determined for optimal placement of the stent in the anatomy so that the clinician can visually detect when the skirt 104 has deformed by that predetermined amount, wherein this amount of deformation will provide the desired placement of the stent relative to the implantation site. As shown, the skirt 104 has a generally circumferential configuration; however, skirt 104 can take a wide variety of shapes. For one example, the skirt 104 can be scalloped and/or have cut-out portions to generally match the three-dimensional shape of the native valve annulus. Additionally, it is contemplated that a stent can include multiple skirts in order to achieve additional sealing and/or to provide additional indications to the clinician of the placement, including axial and/or rotational alignment of the stent.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A replacement prosthetic heart valve for engagement with a structure of an original prosthetic heart valve that comprises a tubular base from which multiple commissure posts extend in an axial direction, wherein at least one of the commissure posts comprises at least one visually detectable commissure marker, the replacement prosthetic heart valve comprising:
a stent structure comprising:
  a generally tubular body portion having a longitudinal axis; and
  at least one visually detectable and directionally distinguishable marker on a portion of the stent structure; and
at least two leaflets attached within the interior area of the tubular body portion of the stent structure;
wherein the at least one visually detectable and directionally distinguishable marker of the stent structure is positionable relative to the at least one visually detectable commissure marker of the original prosthetic heart valve and is directionally distinguishable such that the directionally distinguishable marker appears differently if the directionally distinguishable marker is on a portion of the generally tubular portion towards the viewer than if the directional distinguishable marker is on a portion of the generally tubular portion away from the viewer;
wherein the visually detectable and directionally distinguishable marker of the replacement heart valve is radiopaque; and
wherein the visually detectable and directionally distinguishable marker of the replacement heart valve is c-shaped, wherein the c-shape is transverse to the longitudinal axis and configured to indicate a rotational orientation around the longitudinal axis of the replacement heart valve.

2. The replacement heart valve of claim 1, wherein at least one visually detectable commissure marker of the original heart valve is directionally distinguishable.

3. The replacement heart valve of claim 2, wherein the at least one marker of the replacement heart valve comprises indicia that is the same as the at least one commissure marker of the original prosthetic heart valve.

4. The replacement heart valve of claim 1, wherein at least one of the visually detectable markers is visible with fluoroscopic visualization techniques.

5. The replacement heart valve of claim 1, wherein the replacement heart valve further comprises at least one visually detectable skirt that extends around at least a portion of the generally tubular body portion.

6. The replacement heart valve of claim 5, wherein the at least one skirt comprises a deformable sealing skirt, wherein deformation of the sealing skirt is visually detectable.

7. The replacement heart valve of claim 1, wherein the at least one visually detectable marker of the replacement prosthetic valve comprises multiple markers.

8. A replacement prosthetic heart valve having a longitudinal axis and associated with an original heart valve, wherein the original valve comprises a tubular base from which multiple commissure posts extend in an axial direction and at least one visually detectable marker associated therewith, and wherein the replacement heart valve comprises at least one visually detectable and directionally distinguishable marker that is c-shaped, wherein the c-shape is transverse to the longitudinal axis and alignable with the at least one marker of the original heart valve and directionally distinguishable such that the visually detectable and directionally distinguishable marker appears differently if the visually detectable and directionally distinguishable marker is on a portion of the replacement heart valve towards the viewer than if the visually detectable and directionally distinguishable marker is on a portion of the replacement heart valve away from the viewer, wherein the visually detectable and directionally distinguishable marker of the replacement heart valve is radiopaque, and wherein the visually detectable and directionally distinguishable marker of the replacement heart valve is configured to indicate a rotational orientation around the longitudinal axis of the replacement heart valve.

9. The combination of claim 8, wherein the at least one visually detectable marker of the original heart valve comprises at least one of an annular marker, a one sinus marker, and a commissure marker associated with at least one of the commissure posts.

10. The combination of claim 9, wherein at least one annular marker, or at least one sinus marker, or at least one commissure marker is associated with the original heart valve.

11. The combination of claim 9, wherein at least one annular marker is associated with the original heart valve, and wherein the at least one visually detectable marker of the replacement heart valve comprises a skirt comprising at least one skirt marker for alignment with the at least one annular marker associated with the original heart valve.

12. The combination of claim 9, wherein the at least one visually detectable marker of the replacement heart valve comprises at least one commissure marker for alignment with at least one commissure marker associated with the original heart valve.

13. The combination of claim 8, wherein the at least one visually detectable marker of the replacement valve comprises at least one deformable sealing skirt, wherein deformation of the sealing skirt is visually detectable.

14. A method of implanting a replacement prosthetic heart valve within an original prosthetic heart valve comprising a tubular base from which multiple commissure posts extend in an axial direction, wherein at least one of the commissure posts comprises at least one visually detectable commissure marker, the method comprising:
   positioning a replacement prosthetic heart valve in an internal area defined by a generally tubular structure of the original prosthetic heart valve, wherein the replacement heart valve comprises:
   a stent structure comprising:
      a generally tubular body portion having a longitudinal axis; and
      at least one visually detectable and directionally distinguishable marker on a portion of the stent structure, that is c-shaped, wherein the c-shape is transverse to the longitudinal axis and directionally distinguishable such that the visually detectable and directionally distinguishable marker appears differently if the visually detectable and directionally distinguishable marker is on a portion of the generally tubular portion towards the viewer than if the visually detectable and directionally distinguishable marker is on a portion of the generally tubular portion away from the viewer; and
   at least two leaflets attached within the interior area of the tubular body portion of the stent structure;
   adjusting the location of the replacement heart valve by aligning at least one visually detectable marker of the replacement heart valve with at least one visually detectable commissure marker of the original heart valve,
   wherein the visually detectable and directionally distinguishable marker of the replacement heart valve is radiopaque, and
   wherein the visually detectable and directionally distinguishable marker of the replacement heart valve is configured to indicate a rotational orientation around the longitudinal axis of the replacement heart valve.

15. The replacement heart valve of claim 1, wherein the visually detectable and directionally distinguishable marker of the replacement heart valve extends entirely through a non-radiopaque portion of the stent structure.

16. The combination of claim 8, wherein the visually detectable and directionally distinguishable marker of the replacement heart valve extends entirely through a non-radiopaque portion of the replacement heart valve.

17. The method of claim 14, wherein the visually detectable and directionally distinguishable marker of the replacement heart valve extends entirely through a non-radiopaque portion of the stent structure.

* * * * *